United States Patent [19]

Esmon et al.

[11] Patent Number: 5,135,874
[45] Date of Patent: Aug. 4, 1992

[54] METHOD FOR EVALUATING IMMUNOGENICITY

[75] Inventors: Pamela C. Esmon, Richmond; Michael A. Fournel, Castro Valley, both of Calif.

[73] Assignee: Miles Inc., Elkhart, Ind.

[21] Appl. No.: 493,659

[22] Filed: Mar. 15, 1990

Related U.S. Application Data

[63] Continuation-in-part of Ser. No. 202,177, Jun. 1, 1988.

[51] Int. Cl.$^5$ .......................................... G01N 33/543
[52] U.S. Cl. ................................. 436/518; 436/547; 436/815; 436/821; 436/824; 424/85.8; 530/413; 935/76
[58] Field of Search ............... 436/518, 528, 529, 530, 436/547; 530/387, 380, 383, 413; 424/85.8

[56] References Cited

PUBLICATIONS

Courtney et al., "High-level production of biologically active human α, antitrypsin in *Escherichia coli*", Proc. Natl. Acad. Sci. USA 81:669-673 (Feb. 1984).

Courtney et al., "Synthesis in *E. coli* of α, -antitrypsin variants of therapeutic potential for emphysema and thrombosis," Nature 313:149-151 (10 Jan. 1985).

*Primary Examiner*—Esther L. Kepplinger
*Assistant Examiner*—Carol E. Bidwell
*Attorney, Agent, or Firm*—David J. Aston; Elizabeth F. Enayati

[57] ABSTRACT

A method for evaluating the potential immunogenicity of a protein derived from recombinant DNA technology. The method involves injecting an animal with the recombinant protein and then isolating antiserum from the animal. The antiserum is depleted of antibodies to a reference protein, i.e., a plasma derived protein, by adsorbing the antiserum against the reference protein. The adsorbed antiserum is then blotted against the recombinant protein, to see if any antibodies were produced which recognize the recombinant protein, but did not recognize the plasma-derived protein during adsorption.

6 Claims, 8 Drawing Sheets

METHOD FOR EVALUATING IMMUNOGENICITY

This is a continuation-in-part of Ser. No. 202,177 filed on Jun. 1, 1988.

BACKGROUND OF THE INVENTION

1. Field of the Invention

The present invention relates to the preclinical testing of therapeutic products and, more particularly, to the testing of a protein, intended for repeated administration in humans, for immunogenicity through the use of a protocol involving the use of the immune system of an animal and the comparison of immune responses to a test and a reference protein.

2. Description of the Related Art

With the advent of recombinant DNA technology, a number of therapeutically active peptides have been developed for use in humans. These peptides are coded for by human genes which have been cloned into a host system for production. The host system may be a bacterium, such as *E. coli*, a yeast such as *Saccharomyces cerevisae*, or a mammalian cell line, such as a hybridoma or a continuous cell line such a Chinese Hamster Ovary or Baby Hamster Kidney.

Regardless of the host system chosen, there are questions which may be raised as to the "authenticity" of a peptide product, in terms of its suitability for human use. One such question involves the response of an immunocompetent human host to the therapeutic peptide. This response may in certain instances have clinical significance, such as has been reported in some cases of administration of recombinant human growth hormone (produced in *E. coli*) or in the case of murine monoclonal antibodies. Unfortunately, the human immune response to a therapeutic peptide is impossible to predict with certainty, and little literature exists on the development of animal models which can be used to predict immunogenicity in preclinical testing.

A common method of immunogenicity testing in animals involves repeat administration of final container product and subsequent animal evaluation. Such evaluation may range from observation for anaphylactic reactions to measurement of immune complexes.

This method has several substantial drawbacks. First, it is expected that all peptides beyond approximately 5 kD will elicit an immune response in a non-homologous species. Therefore, the appearance of antibodies in such a protocol is to be expected. The mere quantification of these antibodies is not particularly informative, since comparisons among different peptides and different animals are not meaningful.

Another methodology of relevance is passive cutaneous anaphylaxis (PCA), although this test method is not particularly used for immunogenicity testing per se. This is because it is a passive system and does not measure immune response. In this system, an antibody is administered to a guinea pig intracutaneously. Then, an antigen of interest is administered intravenously, coupled with a blue dye. If antigen-antibody complexes are formed, the complexes and the dye will be extravacised, leading to blue spot(s) at the injection site (s). This method is further described by Ovary, Z. (1958).

A chemotactic assay for immunogenicity is described in U.S. Pat. No. 4,714,674.

Affinity adsorption of rabbit antibody has previously been used to define unique antigenic determinants on cytochrome c homologues from different species (Eng J., Reichlin M.: Fractionation of rabbit anti-horse cytochrome c-I. Mol Immunol 16:225, 1979; Jemmerson R. Margoliash E.: Topographic antigenic determinants on cytochrome c. J Biol Chem 254:12706, 1979), as well as to study antibody cross-reactivity among different species albumins (Kamiyama T.: Immunological cross-reactions and species-specificities of bovine, goat and sheep serum albumins. Immunochemistry 14:85, 1977; Sakata S., Atassi M. Z.: Immunochemistry of serum albumin. VI. A dynamic approach to the immunochemical cross-reactions of proteins using serum albumins from various species as models. Biochimica et Biophysica Acta 576:322, 1979). The use of affinity chromatography to characterize the potential immunogenicity of recombinant Factor VIII and a recombinant Factor VIII deletion mutant have been briefly summarized (Esmon P. C., Mitra I., Fournel M. A.: Recombinant Factor VIII Imunogenicity studies. FASEBJ 2(5)5027, 1988).

SUMMARY OF THE INVENTION

The present invention provides a method for evaluating the immunogenicity of a therapeutic product prior to its use in humans.

The method is particularly well suited for use with therapeutic proteins. The protein of interest, termed herein "PX", for unknown protein or product, is compared to a naturally occurring counterpart, termed herein "PR", for reference product. For example, PX may be a recombinant protein such as alpha-1-proteinase inhibitor, recombinant Factor VIII or variants, or fragments thereof. PR may be plasma derived alpha-1-proteinase inhibitor or plasma derived Factor VIII, respectively.

PX is purified and injected into an animal so that the animal raises antibodies to PX. The rabbit has been found to be particularly well suited for this purpose, as it has a particularly sensitive immune system. The rabbit antiserum is then isolated and adsorbed against PR.

The adsorption protocol has been found to be particularly effective according to the following steps: The PR is coupled to a solid support i.e., a column. The IgG purified from the antiserum is passed over the solid support so that all antibodies to PR in the antiserum are bound to the PR in the support. The adsorbed antibody is tested against PR to verify that no reactivity towards PR remains.

The adsorbed antibody is also tested against PX. This is done according to the Western Blotting procedure in parallel with the testing against PR. The antibody should show no reactivity with PR, due to the previous adsorption.

Any reactivity of the antibody with PX indicates that the animal has produced antibodies against PX which recognize a different epitope on PX than any epitope on PR, otherwise the antibody would have been adsorbed by PR. This means that there exist on PX potentially antigenic sites in comparison to PR, and that the candidate product should be considered as potentially immunogenic in humans. Data have been developed and are presented herein which show both positive and negative results in terms of potential immunogenicity.

While it is possible to use a plasma-derived protein as the immunizing protein, (i.e., PX) it is important to recognize that this would show whether or not there exist epitopes on the plasma-derived protein which do not exist in the recombinant protein (i.e., PR). This is not per se a relevant inquiry in terms of potential immunogenicity in humans.

Furthermore, the present method may employ a panel of monoclonal antibodies in lieu of a polyclonal antibody.

BRIEF DESCRIPTION OF THE DRAWINGS

Protein (1 μg) was applied to each lane and blots were probed with anti-rFVIII 90-142-80 before (Unfractionated) or after (Flow Through Fraction) affinity adsorption with pdFVIII-Sepharose, or with Concanavalin A as described in the Methods.

BRIEF DESCRIPTION OF THE INVENTION

Alpha-1-Proteinase Inhibitor

Alpha-1-Proteinase Inhibitor (Alpha-1-PI; Alpha-1 anti-trypsin) is a 54,000 dalton glycoprotein normally present in human plasma at a concentration of 1.3 mg/mL (Pannell et al, 1974). Individuals with a hereditary deficiency in this neutrophil elastase inhibitor have been shown to have a high disposition for the development of emphysema.

The application of recombinant DNA (rDNA) technology to this protein in recent years has yielded a variety of interesting molecules of potential therapeutic utility. Rosenberg et al (1984) and Courtney et al (1984, 1985) have described the expression of Alpha-1-PI in yeast or E. coli, respectively, and have also described mutant forms of the molecule with biochemical properties distinct from the native form which have potential therapeutic significance.

Such rDNA Alpha-1-PI molecules have sequence homology to the native form but lack glycosylation (which accounts for 14% of the mass of the plasma-derived molecule). Although the functional significance of carbohydrate in plasma proteins remains unclear, recent evidence has indicated the circulating half-life of non-glycosylated forms of this molecule in animals is substantially shorter than that obtained with the plasma-derived form (Travis et al, 1985).

The present example was undertaken to evaluate the potential immunogenicity of the molecule to determine if unique epitopes might exist in the molecules which lack carbohydrate but are sequentially homologous with the native human plasma molecule.

MATERIALS AND METHODS

Alpha-1-PI Proteins. rDNA derived Alpha-1-PI was synthesized in yeast as described by Rosenberg et al (1984); both MET358 (the native protein sequence) and VAL358 (an alpha-1-proteinase inhibitor variant containing a valine instead of a methionine at position 358) forms of the molecule were used. Subsequent purification was accomplished by methods essentially as described by Janoff et al (1986) and material was stored at +4 C. or frozen until use. Human plasma-derived Alpha-1-PI was initially purified as described by Coan et al (1985) and further purified to homogeneity by the method of Glaser et al (1982); purity of greater than 95% was demonstrated by specific activity and SDS-PAGE analysis.

Alpha-1-PI antigen was quantitated employing a sandwich ELISA technique similar to that described by Revak et al (1985) in which an immunopurified rabbit anti-human Alpha-1-PI antibody was used. F (ab')$_2$ of the antibody was used to coat microtiter wells; once non-specific binding was blocked with bovine serum albumin, test samples were added followed by incubation with intact antibody. Detection was accomplished with a Protein-A-horseradish peroxidase conjugate (Boehringer Mannhein Biochemicals) and addition of a specific colorimetric reagent, 2,2'-azino-di(3-ethylbenzthiazoline sulfonic acid) (ABTS; Sigma), stopping the reaction with 5% sodium dodecyl sulfate; color development quantitation was accomplished in a Dynatech ELISA Reader.

Electrophoresis was performed in 8% polyacrylamide gels with sodium dodecyl sulfate treated samples (SDS-PAGE) according to Laemmli (1970) and stained by the silver nitrate method of Morrissey et al (1981). Western blotting analysis was performed essentially according to Renart et al (1979).

Passive cutaneous anaphylaxis assay was performed in guinea pigs as described by Gervoy J. S. et al (1977) Methods in Immunol 445-458.

EXPERIMENTAL

Polyclonal antisera to both rDNA derived proteins (MET and VAL) and a non-transfected yeast extract were separately raised in groups of three New Zealand White rabbits (2-4 kg, male) by repeated subcutaneous injection of the subject protein emulsified in Freund's complete (initial injection) or incomplete adjuvant. Development of antibody was assessed by precipitin formation in agar gel and harvest of immune serum accomplished. Gamma-globulin fractions were prepared by DEAE-Sepharose ® (Pharmacia) chromatography. Following coupling of human plasma-derived Alpha-1-PI to CNBr-Sepharose (Pharmacia) at a load of 5 mg/mL gel, adsorption of the specific gamma-globulin was accomplished by cycling the respective protein gamma globulin fraction through the column of human Alpha-1-PI-Sepharose in a 5 mM Tris+0.15M NaCl buffer, pH 7.4. Specifically bound antibody ("Bound Fraction") was subsequently eluted with 1M propionic acid in the Tris-saline buffer, pH 3.5 and collected into solid Tris to return the pH to 7.0-7.4. Cycling in this fashion persisted until no significant $A_{280}$ increase was obtained in the propionic acid elution step. The "Flow Through Fraction" represents antibody that did not bind to the affinity column. All resulting fractions were stored at $-20°$ C. until use.

Figure 1:
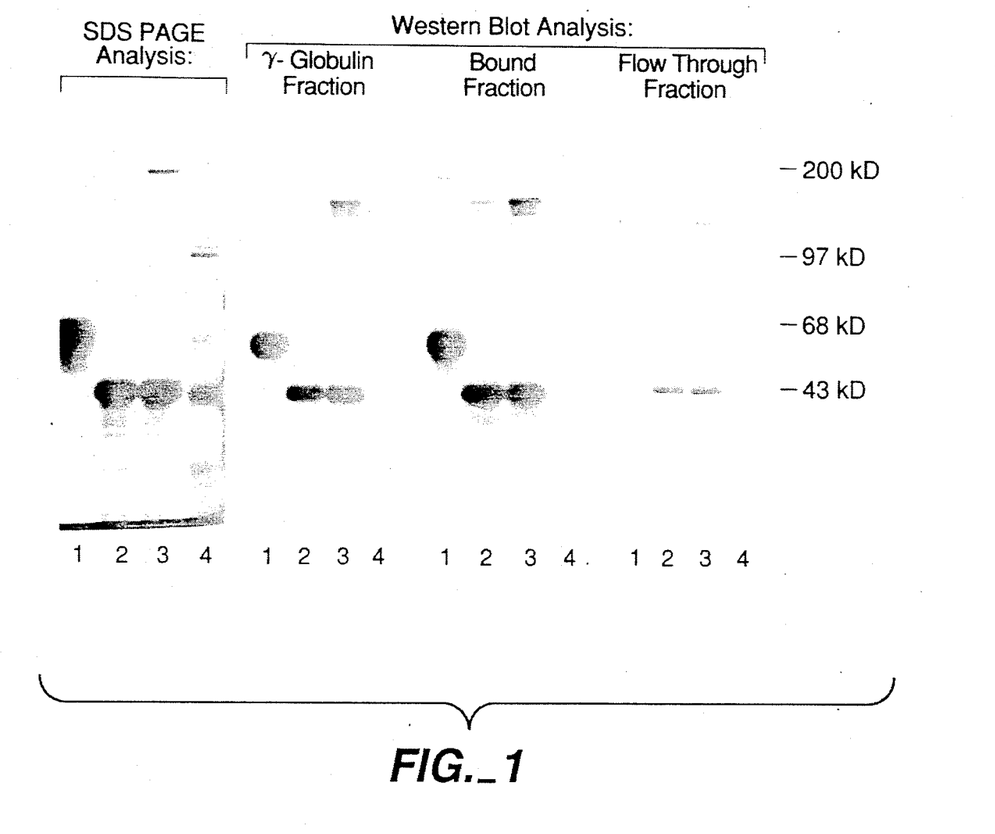
FIG. 1 is an SDS-PAGE and a Western Blot Analysis of plasma derived and recombinant Alpha-1-proteinase inhibitor, 1 μg protein was applied to each lane.

Antibody raised in rabbits against each rDNA-Alpha-1-PI protein was subjected to repetitive adsorption against plasma-derived Alpha-1-PI immobilized on CNBr-Sepharose, as described above. The resulting antibody fractions were then used to probe nitrocellulose membranes to which had been transferred all three proteins as well as a yeast extract. FIG. 1 presents the results obtained in such an experiment with the rabbit-anti-rDNA-VAL358-Alpha-1-PI antibody fractions.

In FIG. 1, each lane corresponds to the following preparations: (1) plasma derived (pd) Alpha-1-PI; (2) rDNA-MET-Alpha-1-PI; (3) rDNA-VAL-Alpha-1-PI; and (4) yeast extract. Molecular weights are determined from pre-stained markers. The first panel in FIG. 1 represents the SDS PAGE patterns of each sample after silver staining. The second panel represents the Western blot using the gamma globulin fraction of pooled antisera from rabbits, each rabbit having been immunized with rDNA-VAL Alpha-1-PI.

This unfractionated gamma globulin was able to recognize both rDNA proteins and the plasma-derived molecule, including some high molecular weight aggregates; note the absence of recognition of a major yeast extract protein band seen in the SDS-PAGE gel with a molecular weight apparently similar to either rDNA derived Alpha-1-PI protein (mobility difference from plasma-derived Alpha-1-PI presumably due to absence of glycosylation).

The BOUND fraction (third panel) similarly recognizes all three Alpha-1-PI species, but the FLOW THROUGH FRACTION, fourth panel, (i.e., that gamma globulin which did not bind to plasma-derived Alpha-1-PI Sepharose) failed to blot the plasma-derived protein but still quite strongly recognized both rDNA derived Alpha-1-PI molecules (as well as a higher molecular weight yeast extract protein). The recognition of the MET-Alpha-1-PI by this antibody suggests that unique antigen(s) were not due to the single amino acid substitution found in the VAL variant. Similar results were obtained when rabbit-anti-rDNA- MET358-Alpha-1-PI antibody was subjected to this protocol. These results were also confirmed for both antibody preparations in passive cutaneous anaphylaxis analyses in which significant reaction was seen with either FLOW THROUGH fraction with both rDNA derived Alpha-1-PI proteins but not with plasma-derived Alpha-1-PI.

The present study suggests that if the rabbit could distinguish unique determinants on rDNA derived proteins from the corresponding plasma-derived protein, then it would be likely that a human recipient would also and thus might be expected to generate antibodies against those unique sites (but not to shared determinants). The results obtained clearly suggest the presence of such unique epitopes in both rDNA derived proteins, presumably independent of the active site substitutions. While these studies have used adjuvant stimulation and sub-cutaneous inoculation to achieve maximal antibody formation, the conclusion that unique determinants apparently exist on either rDNA derived molecule present at least the possibility of a similar recognition in humans.

It should also be noted that the present series of experiments evaluated two different rDNA proteins having single amino acid substitutions. The present process would also be useful in the evaluation of a protein analogue in reference to a standard or native "reference protein" containing the native amino acid sequence.

FACTOR VIII

The first part of this study was done with recombinant DNA-derived Factor VIII (rFVIII as described in Vehar et al. "Structure of Human Factor VIII," Nature 312:337-342 (1984) and Eaton et al., "Characterization of Recombinant Human Factor VIII," J. Biol. Chem. 262(7) 3285-3290 (1987)). This material is shown in lane 2, FIG. 2, which is a silver-stained 4-12% SDS PAGE. Lane 1 of FIG. 2 contains similar purified plasma derived Factor VIII (pd FVIII). Lane 3 contains a control protein, chicken serum albumin, obtained from Sigma Chemical Co. The second part of the study was performed using a rFVIII deletion mutant rFVIII des-797-1562 (referred to here as rFVIII 90-142-80) which lacks amino acids 797 through 1562, leaving the 90 kDa fragment, 142 amino acids of the B region (56 on the N-terminal side of the deletion site and 86 on the C-terminal side) and the 80 kDa fragment (Eaton D. L., Wood W. I., Eaton D., Hass P. E., Hollingshead P., Wion K., Mather J., Lawn R. M., Vehar G. A., Gorman C.: Construction and characterization of an active Factor VIII variant lacking the central one-third of the molecule. Biochemistry 25:8343, 1986). To test for the presence of potential immunogenic epitopes in rFVIII, antibody to rFVIII was raised in rabbits as described below. This antibody then was analyzed for antibody that would not cross-react with pdFVIII. To perform this task, rabbit anti-rFVIII (RαrFVIII) antibody was first adsorbed using two different affinity columns designed to remove antibody directed toward proteins known to contaminate rFVIII. Antibody to host cell protein contaminants was removed by adsorption against a preparation designated "SHAM 3". SHAM 3 is a protein mixture derived from the culture supernatant of non-FVIII secreting host cells after the supernatant was subjected to the first step in rFVIII purification (i.e., a DEAE column). Antibody to media constituents was similarly removed by adsorption against an $\alpha+\beta$ globulin fraction derived from media protein supplement.

Antibody Preparation: Groups of three New Zealand White rabbits were immunized subcutaneously with 1 mL of an emulsion of 70 μg/mL rFVIII plus 7 μg/mL chicken albumin (or 70 μg/mL rFVIII 90-142-80) in Freunds complete adjuvant and were boosted weekly for five weeks with the same antigens in Freunds incomplete adjuvant. After six weeks, plasma was collected and converted to serum. To prepare IgG, serum was diluted 1:3 with distilled water, applied to a DEAE-Sepharose column equilibrated in 5 mM Tris pH 8.0 and the unbound fraction was collected, pooled and concentrated using an Amicon apparatus.

Antibody Adsorption: Affinity columns were produced by linking antigen to CNBR-Sepharose according to the Pharmacia protocol or by linking to controlled pore glass. The ratio of protein to resin for each column was as follows: 6 mg SHAM 3 per 1.5 g CPG, 10 mg $\alpha+\beta$ globulin per 2 g CNBR-Sepharose and 1 mg pdFVIII per 1 g CNBR-Sepharose. Following coupling, each resin was poured into a 1×10 cm column. All chromatography steps were performed with the assistance of a Pharmacia FPLC system. Resin was first equilibrated in 0.5M NaCl, 20 mM Tris, pH 7.5 (TBS), then sample was applied at a flow rate of 0.1 mL/min (7.6 mL cm$^{-2}$hr$^{-1}$). The column was washed with TBS until the absorbance at 280 nm returned to baseline at which time the direction of buffer flow through the column was reversed. The flow rate was increased to 0.25 mL/min (19.0 mL cm$^{-2}$hr$^{-1}$) and the column was washed again until the absorbance returned to baseline. The column eluant collected to this point was pooled and concentrated to 3 to 5 mL using an Amicon concentrator. This fraction was either reapplied to the affinity column or saved for further analysis and it is referred to as the "Flow Through" fraction. To elute bound antibody, the column was washed with 1M propionic acid in TBS until the absorbance at 280 nm reached a stable value. Prior to reapplication of sample, the column was washed with TBS until the pH returned to 7.5.

Electrophoretic Procedures: SDS-PAGE was performed on reduced, denatured samples using 4 to 12% acrylamide gradient gels according to Laemmli; all procedures were carried out at room temperature. Gels were silver stained (Morrissey, 1981), or they were transferred electrophoretically overnight to nitrocellulose filters for Western immunoblotting (Towbin, 1984). Filters were blocked with 2% non-fat dry milk in TBS for 2 hours, then were probed with 10 mL of 5 μg/mL antibody in 2% milk in TBS. Filters were washed 3 times with 0.05% Tween 20 in TBS (TTBS) for 10 minutes, incubated for 2 hours with goat anti-rabbit antibody conjugated to horseradish peroxidase (Biorad) diluted 1:1000 with 2% milk in TBS, washed as above and stained according to the manufacturer's instructions.

Assays: Dot blot immunoassay was performed by spotting 1 μL (64 ng) antigen onto a nitrocellulose membrane that had been pre-wet with TBS and allowed to dry. Antigen was diluted in SDS-sample buffer and boiled for 3 minutes (denatured) or it was diluted in TBS (native). After air drying, the membrane was incubated for 1 hour at room temperature in 5% milk in TBS with shaking. The membrane was then washed 3 times with distilled water and 3 times with TTBS using 5 minute washing steps. The membrane was again air-dried, spotted with 1 μL of serial dilutions of antibodies to be tested (diluted with 20 mM Tris, pH 8, 0.5M NaCl, 0.5% Tween 80, 0.01% Thimerosal) and air-dried again. Membrane was then incubated 2 hours with goat anti-rabbit antibody conjugated to alkaline phosphatase (Biorad) diluted 1:5000 in 5% milk in TBS and washed 1 time with water, 3 times with TTBS and 2 times with TBS, using 5 minute washing steps. Alkaline phosphatase assays were performed by cutting the membrane into squares containing a single dot, then incubating each 1 cm square in 0.5 mL of 1 mg/mL p-nitrophenyl phosphate, 0.1M Tris, 1 mM MgCl$_2$, pH 8.8 for 16 to 18 hours at room temperature. Samples were then pipetted into microtiter plate wells and the absorbance at 410 nm was determined with the air of an MR 600 Dynatech micro-plate reader. Background signal obtained in the absence of antigen was subtracted from each assay value.

Protein was measured by the Pierce BCA assay kit according to the manufacturer's instructions.

Thrombin, N-Glyconase Treatments: For thrombin treatment, 10 μg rFVIII 90-142-80 was incubated with 0.1 unit human thrombin for 1 minute at 37° C. in 160 μL 50 mM Tris, pH 7.5, 0.15M NaCl, 2.5 mM CaCl$_2$. 5% glycerol. SDS-PAGE sample buffer was then added, the mixture was boiled to stop the reaction and the samples were subjected to Western immunoblot analysis. For carbohydrate removal, 20 μg rFVIII 90-142-80 was denatured by boiling in 125 μL 0.5% SDS plus 0.1M 2-mercaptoethanol. This solution was diluted 1.5-fold with 0.2M Tris, pH 8.8, 50 mM EDTA, 1.2% Nonidet-P 40, then 1.25 units N-glyconase were added. Following incubation at 37° C. for 19 hours, the reaction was stopped and the proteolytic FVIII fragments analyzed as above.

Lectin and Immunoblotting Procedures: Reduced and denatured proteins were resolved using SDS-PAGE (Laemmli V.K.: Cleavage of structural proteins during the assembly of the head of bacteriophage T4. Nature 227:680 (1970)) with 4 to 12% acrylamide gradient gels, then were transferred to nitrocellulose filters for Western immunoblotting (Towbin H., Staehelin T., Gordon J.: Electrophoretic transfer of proteins from polyacrylamide gels to nitrocellulose sheets: procedure and some applications. Proc Natl Acad Sci 76:4350, 1979). Non-specific binding sites were blocked by incubating filters in TBS containing 2% non-fat dry milk for 2 hours, then filters were probed with 10 mL 5 μg/mL polyclonal or 1 μg/mL monoclonal antibody in TBS plus 2% non-fat dry milk. Nitrocellulose filters were washed 3 times with 0.05% Tween 20 in TBS (TTBS) for 10 minutes with shaking, incubated for 2 hours with goat anti-rabbit antibody conjugated to horseradish peroxidase (diluted 1:1000 with 2% milk in TBS), washed as above and stained according to the manufacturer's instructions.

For peptide competition experiments, either bradykinin or the deletion site peptide was solubilized by boiling in TBS containing 2% SDS, and precipitate was removed by passing the solution through a 0.2 micron filter. Peptide concentration was 0.2 mg/mL as determined by BCA assay. Varying amounts of peptide were incubated with antibody in TBS containing 2% non-fat dry milk at 4° C. for 18 hours: these solution were then used to probe nitrocellulose filters as described above.

For lectin blotting, all buffers contained 10 mM MnCl$_2$, 10 mM CaCl$_2$. Nitrocellulose filters were blocked for 2 hours with TBS containing 2.5% HSA, washed 3 times with TTBS for 10 minutes, incubated for 1 hour with 10 μg/mL Concanavalin A-biotin in TTBS, then washed as above. For detection, filters were incubated for 30 minutes with streptavidin-horseradish peroxidase in TTBS (1:2000 dilution), washed as above, then subjected to the Biorad horseradish peroxidase color development procedure.

EXPERIMENTAL

RαrFVIII (20 mg) was passed 5 times over SHAM 3 conjugated to CPG, then 5 times over α+β globulin conjugated to Sepharose. See Table 1.

TABLE 1

ANTIBODY ADSORPTION: NUMBER OF PASSES OVER EACH AFFINITY COLUMN

| AFFINITY COLUMN | | ANTIBODY REFERENCE NUMBER | | |
|---|---|---|---|---|
| Antigen | mg | 3712-38 | 3712-39 | 3712-52 |
| SHAM 3 | 6 mg | 5 | 5 | 5 |
| α + β Globulin | 10 mg | | 5 | 5 |
| pdFVIII | 1 mg | | | 12 |

Figure 3:
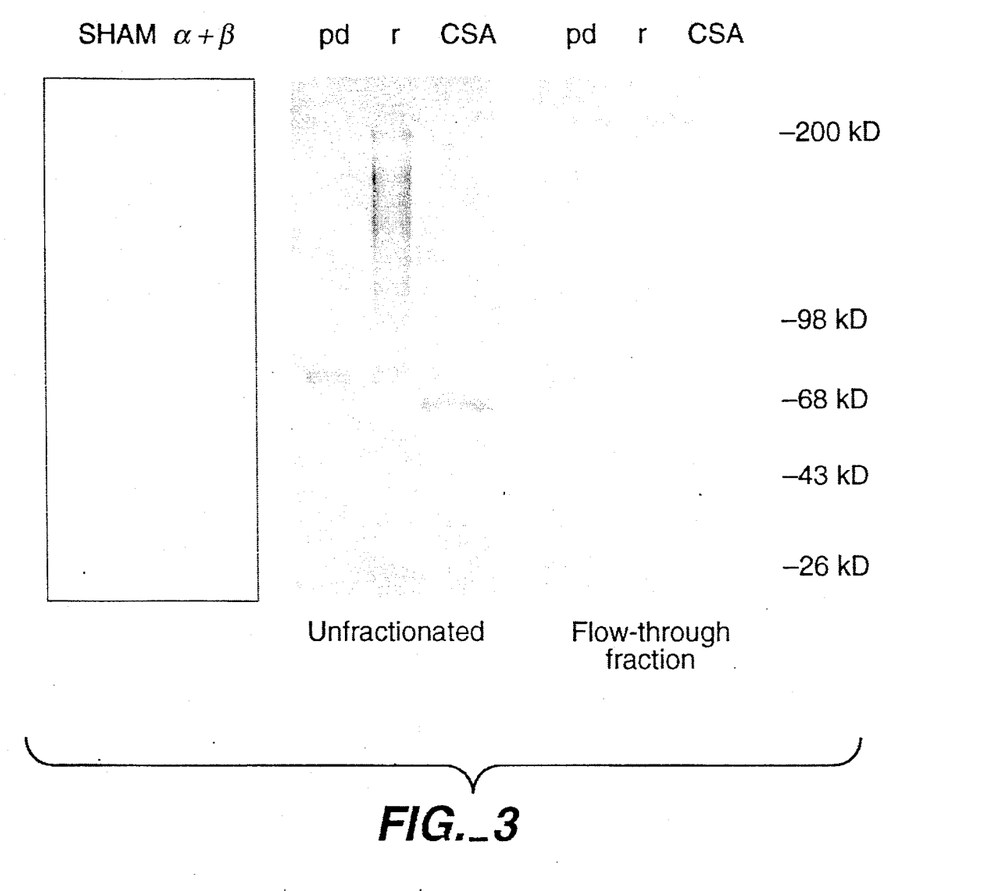
FIG. 3 is a Western Blot analysis of anti-rFVIII antibody. Filters were probed with the indicated antibody. Protein per lane: 1 μg rFVIII, 1 μg chicken serum albumin, 10 μg SHAM 3 (Host cell protein), 10 μg alpha plus beta globulin (media protein).

The resulting antibody (3712-39) did not cross-react with either SHAM 3 or α+β globulin when analyzed by a Western immunoblotting procedure, shown in FIG. 3, panel 1. Lane 1, pd, is pd FVIII; r is rFVIII; CSA is chicken serum albumin. When probed with antiserum 3712-39, antibodies to rFVIII, pdFVIII and CSA (with which the rabbits were also immunized) produced detectable bands against their respective antigens.

To remove anti-FVIII antibody capable of cross-reacting with pdFVIII, the reference product in this example, antibody 3712-39 was passed 12 times over pdFVIII conjugated to Sepharose. Western immunoblot analysis of the resulting antibody (3712-52) indicated that all antibody capable of cross-reacting with pdFVIII had been adsorbed. As shown in FIG. 3, panel 3, the adsorbed antiserum did not react with pdFVIII (pd) or rFVIII (r), indicating that all antibody capable of recognizing rFVIII was adsorbed by pdFVIII.

Although the rabbits immunized with rFVIII were also immunized with chicken serum albumin (CSA), antibody to this protein (3712-52) was not removed during the affinity chromatography steps (FIG. 3), indicating that FVIII antibody adsorption was specific.

A variation of the standard dot blot immunoassay was also used in this study in order to quantify the FVIII-specific antibody remaining after pdFVIII adsorption (Table 2).

TABLE 2

QUANTITATIVE DOT BLOT

| ANTIGEN | | ANTIBODY DETECTED IN FLOW-THROUGH FRACTION (% UNFRACTIONATED ± SD) |
|---|---|---|
| Denatured | pdFVIII | 3.1 ± 5.3 |
| | rFVIII | 4.9 ± 4.1 |
| Native | pdFVIII | 7.9 ± 3.8 |
| | rFVIII | 5.0 ± 2.9 |

This assay is similar to a reverse ELISA in that the antigen concentration remains constant while the antibody concentration is variable, allowing one to quantitate antibody specific for a given antigen. Analysis of antibody before and after pdFVIII adsorption using denatured pdFVIII showed that the FVIII-specific antibody had been adsorbed. Similar results were seen for denatured rFVIII as well as for native pdFVIII and rFVIII.

Recovery of IgG through the adsorption steps as measured by total protein is shown in Table 3. Although approximately 90% of the antibody was recovered after each cycle, the large number of passes required for complete antibody removal resulted in low recovery values.

TABLE 3

ANTIBODY RECOVERY AFTER EACH AFFINITY COLUMN

| COLUMN | PROTEIN RECOVERED % TOTAL |
|---|---|
| SHAM 3 | 87 |
| α + β Globulin | 56 |
| pdFVIII | 18 |

In this example, antibody was raised to rFVIII and tested for the presence of antibody that would recognize rFVIII, but not pdFVIII. This putative rFVIII-specific antibody should not bind to a pdFVIII affinity column, therefore, after removing antibody directed to non-FVIII protein, animal antibody was contacted with pdFVIII by adsorption with pdFVIII conjugated to Sepharose. Western immunoblot analysis showed that adsorption removed all antibody capable of recognizing pdFVIII as well as that capable of recognizing rFVIII (FIG. 3), indicating that no rFVIII-specific antibody could be detected. Antibody adsorbed with pdFVIII was also analyzed by dot blot immunoassay. When either denatured or native, rFVIII or pdFVIII was used as the capture antigen, native antigens gave slightly higher values than denatured antigens, but there was not a significant difference in the values obtained for rFVIII compared to pdFVIII, showing that rFVIII-specific antibody was not detected (Table 2). The lack of such antibody is consistent with the notion that rFVIII does not contain unique epitopes compared to pdFVIII.

Figure 2:
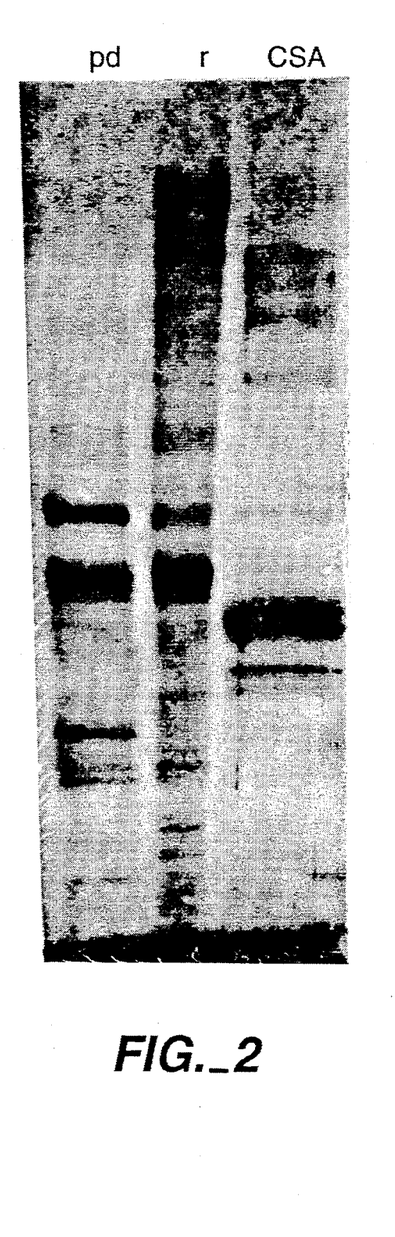
FIG. 2 is a Silver Stained SDS-PAGE Analysis of plasma-derived (pd) and recombinant (r) Factor VIII, with chicken serum albumin (CSA) used as a control.

In the present practice of this invention, multiple passes over each affinity column are required for complete antibody adsorption. Both SHAM 3 and α+β globulin columns required 5 cycles for complete adsorption, while pdFVIII required 12 cycles. Since the pdFVIII affinity column contains less protein per unit resin than either the SHAM 3 or the α+β globulin columns (Table 1), this is to be expected. The large number of cycles caused the final antibody yield to be quite low (Table 2). However, apparent adsorption of FVIII-specific antibody can not be attributed to low antibody yields, since pdFVIII adsorbed antibody (3712-52) still retained ability to react with chicken albumin (FIG. 2).

Figure 4:
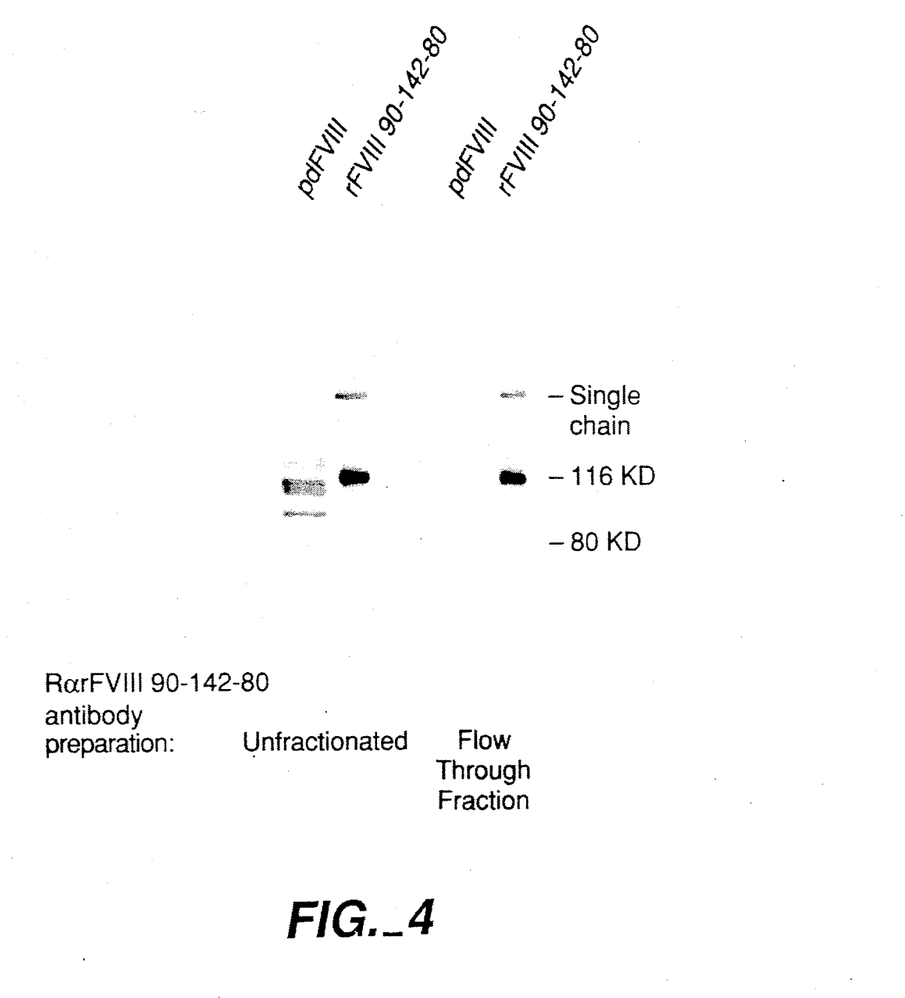
FIG. 4 is a Western blot analysis of anti-rFVIII 90-142-80. Anti-rFVIII 90-142-80 IgG was used to probe Western blots either before (Unfractionated) or after (Flow Through Fraction) affinity adsorption with pdFVIII-Sepharose. pdFVIII (1 μg) or rFVIII 90-142-80 (0.1 μg) were applied to each lane as indicated.

Antibody raised to rFVIII 90-142-80 was also analyzed by affinity adsorption studies. Western immunoblot analysis showed that this antibody did not recognize sham protein (data not shown), so it was not subjected to sham protein-Sepharose affinity chromatography. The signal attained for rFVIII 90-142-80 by Western blot analysis using anti-rFVIII 90-142-80 was much greater than that seen for pdFVIII, so the following analyses were performed using 10-fold less rFVIII 90-142-80 per lane than pdFVIII. Adsorption of anti-rFVIII 90-142-80 IgG with pdFVIII-Sepharose reduced reactivity with pdFVIII as detected by Western immunoblot analysis sufficiently that after 10 passes, no signal was apparent (FIG. 4). In contrast, adsorption of anti-rFVIII 90-142-80 with pdFVIII-Sepharose had little effect on reactivity with rFVIII 90-142-80 (FIG. 4), showing again that a portion of the antibody elicited by rFVIII 90-142-80 recognized determinants not present on pdFVIII.

Figure 5:
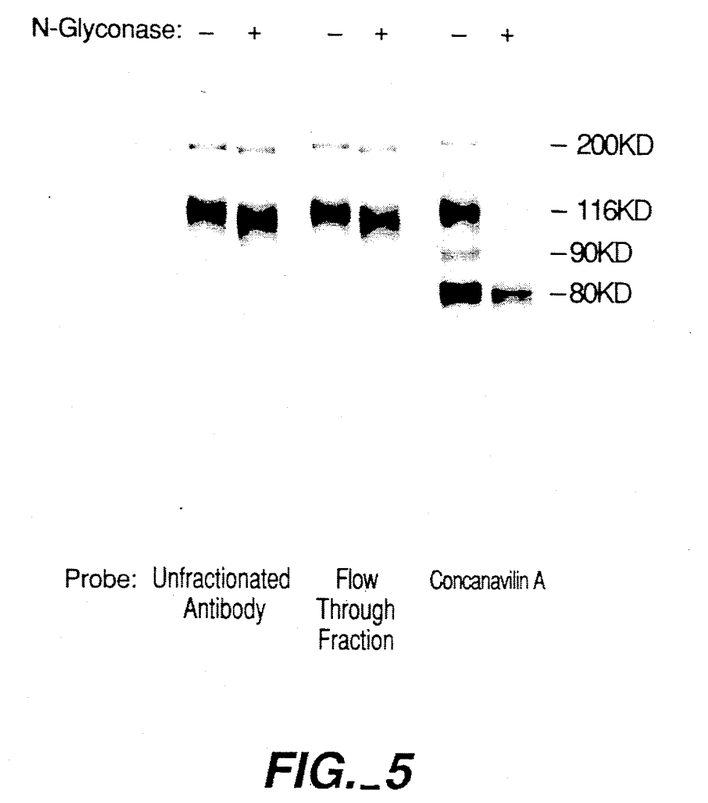
FIG. 5 is a treatment of rFVIII 90-142-80 with N-glyconase. rFVIII 90-142-80 was treated with N-glyconase as described in the Methods (+) or was incubated under similar conditions in the absence of N-glyconase (−).

The presence of antibody specific for rFVIII 90-142-80 prompted a search for epitopes recognized by this antibody. Since FVIII is glycosylated, rFVIII 90-142-80 was treated with N-glycanase to enzymatically remove asparagine-linked oligosaccharides. N-glyconase-treated rFVIII 90-142-80 bound less Concanavalin A than untreated rFVIII 90-142-80 when subjected to lectin blot analysis (FIG. 5), indicating that the amount of carbohydrate on the protein (especially the 200 kDa and 116 kDa fragments) had been reduced. Anti-rFVIII 90-142-80 adsorbed with pdFVIII-Sepharose was then used to examine untreated or N-glyconase-treated rFVIII 90-142-80 (FIG. 5). Treatment with N-glycanase did not appreciably alter the apparent binding of adsorbed or unadsorbed antibody to rFVIII 90-142-80, suggesting that asparagine-linked oligosaccharides do not represent the primary epitope(s) recognized by anti-rFVIII 90-142-80 adsorbed with pdFVIII-Sepharose.

Figure 6:
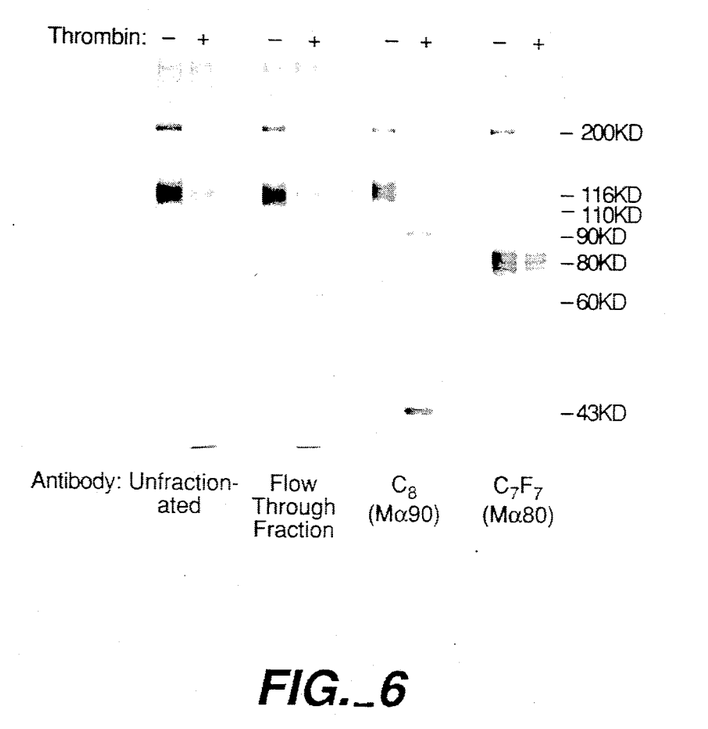
FIG. 6 is a digestion of rFVIII 90-142-80 with thrombin. rFVIII 90-142-80 was digested with thrombin as described in the Methods (+) or was incubated under similar conditions in the absence of thrombin (−). Protein (1 μg) was applied to each lane as indicated and blots were probed with anti-rFVIII 90-142-80 before (Unfractionated) or after (Flow Through Fraction) affinity adsorption with pdFVIII-Sepharose, or with monoclonal antibodies $C_8$ or $C_7F_7$ as indicated.
Figure 7:
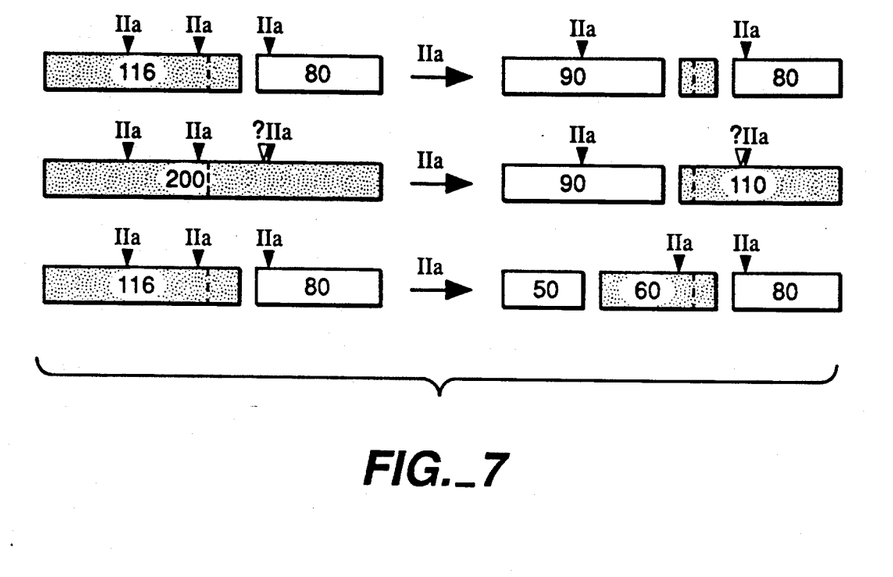
FIG. 7 is a schematic of rFVIII 90-142-80 thrombin fragments. Derivation of the various thrombin cleavage products from rFVIII 90-142-80 is shown schematically. IIa represents thrombin cleavage sites, numbers represent apparent molecular weights by SDS-PAGE and stippled areas represent fragments that react with anti-rFVIII 90-142-80 after affinity adsorption with pdFVIII-Sepharose. Not all possible thrombin fragments are shown, evidence for the origin of the 60 kDa fragment remains circumstantial.

To map the location of epitopes recognized by anti-rFVIII 90-142-80 antibody adsorbed with pdFVIII-Sepharose, thrombin cleavage fragments of rFVIII 90-142-80 were generated and tested for ability to bind adsorbed antibody. Thrombin cleavage products were identified by Western immunoblot analysis using two anti-FVIII monoclonal antibodies. As expected, monoclonal antibody $C_8$ reacted with the 116 kDa, 90 kDa and 43 kDa fragments (recognizes 43 kDa fragment) (Rotblat F., Goodall A. H., O'Brien D. P., Rawlings E., Middleton S., Tuddenham E. G. D.: Monoclonal antibodies to human procoagulant Factor VIII. J Lab Clin Med 101:736, 1983) and monoclonal antibody $C_7F_7$ reacted with the 80 kDa fragment, which it is known to recognize (Wood W. I., Capon D. J., Simonsen C. C., Eaton D. L., Gitschier J., Keyt B., Seeburg P. H., Smith D. H., Hollingshead P., Wion K. L., Delwart E., Tuddenham E. G. D., Vehar G. A., Lawn R. M.: Expression of active human Factor VIII from recombinant DNA clones. Nature 312:330, 1984), as well as a 110 kDa fragment (FIG. 6). Reaction of the 116 kDa and 110 kDa fragments with these monoclonal antibodies indicated that in addition to the 90 kDa or 80 kDa fragments, they contained a portion of the B region. When they were probed with anti-rFVIII that had been adsorbed with pdFVIII-Sepharose, neither the 90 kD now the 80 kDa fragment showed reactivity, while the 116 kDa and 110 kDa fragments did (FIG. 6). This suggested that rFVIII 90-142-80-specific epitopes identified by Western immunoblot analysis resided in the stretch of amino acids linking the 90 kDa and 80 kDa fragments. A 60 kDa fragment also reacted with adsorbed antibody. Since this fragment reacted weakly with $C_8$, it may represent the 43 kDa fragment plus the B region. The arrangement of cleavage fragments within rFVIII 90-142-80 as well as the proposed location of unique epitopes is shown schematically in FIG. 7.

Figure 8A:
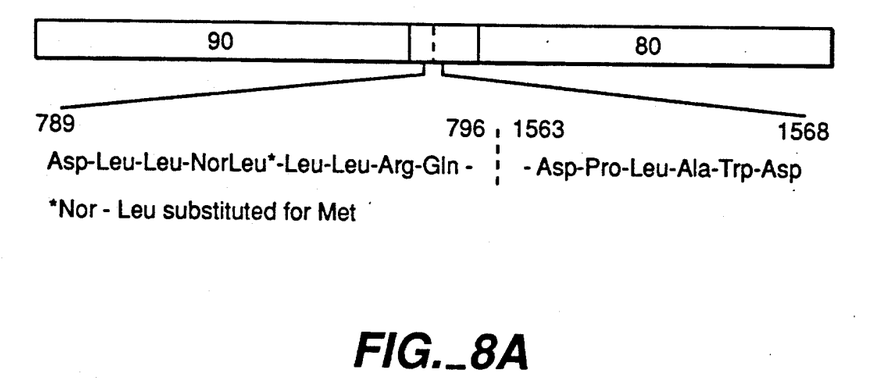
FIG. 8A is a schematic representation of sequence of the deletion site peptide as well as its location within rFVIII 90-142-80. The vertical dotted line represents the deletion site within rFVIII 90-142-80. Note that nor-leucine was substituted for methionine in the peptide.
Figure 8B:
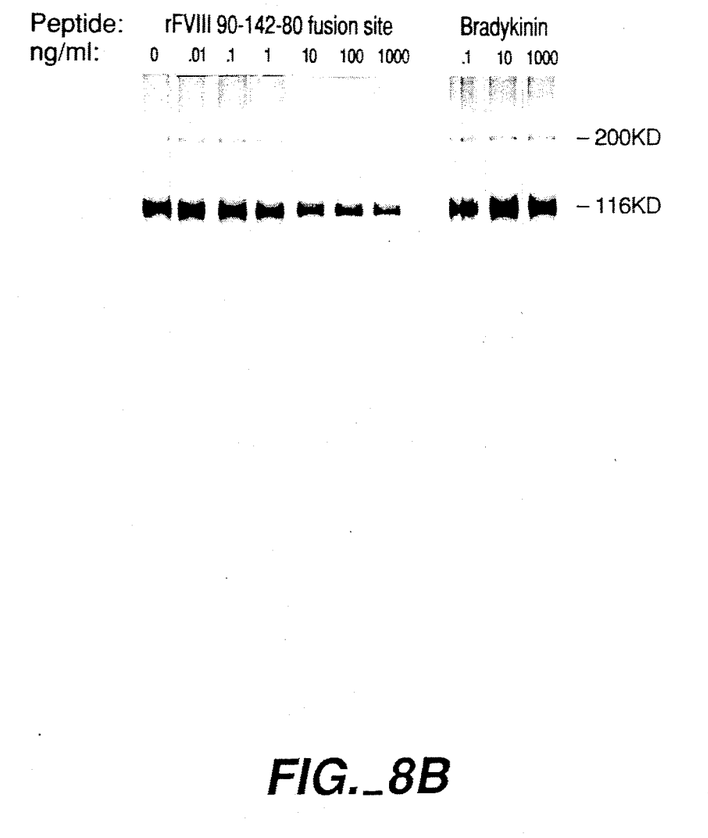
FIG. 8B is an antibody competition using the deletion site peptide. Various amounts of this peptide or bradykinin (as indicated) were incubated as described in the methods with 5 μg/ml (66 nM antibody combining site) anti-rFVIII 90-142-80 that had been adsorbed with pdFVIII-Sepharose. These solutions were then used to probe Western blots containing 0.1 μg rFVIII 90-142-80 per lane.

The coincident location of rFVIII 90-142-80-specific epitopes and the protein's deletion site within the intervening sequence suggested that the deletion site could represent a rFVIII 90-142-80-specific epitope. To explore this notion, a 14 amino acid peptide representing the region surrounding the deletion site was constructed. When varying concentrations of this peptide were used to compete for adsorbed antibody binding to rFVIII 90-142-80, a decrease in intensity was observed by Western immunoblot analysis at a peptide concentration of 10 to 100 ng/mL, corresponding to 0.6 to 6 nM peptide (FIG. 8). Comparable amounts of the 9 amino acid peptide bradykinin did not show any effect. This data is consistent with the notion that the rFVIII 90-142-80 deletion site represents at least one of the rFVIII 90-142-80-specific antibody binding sites that is detected by Western immunoblot analysis.

There are several assumptions built into this immunogenicity test system that need to be clarified. First of all, it is assumed that epitopes distinguished by the human immune system will be detected by the rabbit immune system. Other reference animals may be used in appropriate circumstances in the evaluation of other products. Also, relevant conformational epitopes on the product to be evaluated must not be destroyed by the procedure used to immunize the animal. Evidence that RαrFVIII recognizes many rFVIII epitopes comes from our characterization of the antibody. RαrFVIII is neutralizing and is capable of detecting all polypeptides recognized by any monoclonal or polyclonal antibody we have evaluated (including antibody from FVIII inhibitor patients), especially in ELISA systems for which it serves as a capture antibody. To increase the chance that antibody would be raised to all epitopes, three rabbits were immunized with rFVIII and adsorption studies were performed on a pool of sera from these animals. This should have optimized the yield of antibody directed against all possible rFVIII epitopes. A final assumption is that epitope-specific antibody will be detected by our assay systems. Our initial assay system, Western blot analysis, was chosen because it provided a sensitive antibody assay and allowed for characterization of antibody specificity. Dot blot immunoassay was also used because it allowed quantitation of the FVIII-specific antibody remaining after adsorption and it permitted testing for antibody recognizing native FVIII conformational epitopes. By using such detection systems, the ability to detect unique epitope-specific antibody should have been maximized.

Despite these potential problems, the immunoadsorption assay system was able to distinguish between pdFVIII and the rFVIII deletion mutant rFVIII 90-142-80. These proteins have the same amino acid sequence except for a new gln-asp bond that is created at the deletion site. It is unlikely that the distinction between these proteins is based on conformational epitope(s) because Western blot detection revealed differences between them. Further studies using Western blot analysis suggest that rFVIII 90-142-80- specific epitope(s) are not comprised of carbohydrate moieties, but may instead reside within the B-region. Fragments of rFVIII 90-142-80 (generated by thrombin cleavage) showed differential reaction with the adsorbed anti-rFVIII 90-142-80 antibody indicating that the fragment comprising the remaining B region was immunogenic while the fragments that did not contain the B region were not. Competition with a peptide representing the deletion site also reduced rFVIII 90-142-80-specific antibody binding at a peptide to antibody molar ratio of one to ten but did not abolish it. Residual binding may result from the presence of other novel epitopes in rFVIII 90-142-80 or from the inability of the peptide to attain certain conformations in solution (Berzofsky J. A.: Intrinsic and extrinsic factors in protein antigenic structure. Science 229:932,1985). The ability of the deletion site peptide to compete with the rFVIII 90-142-80-specific antibody for binding indicates that the deletion site represents a novel epitope on rFVIII 90-142-80. Future design of deletion mutants destined for therapeutic use should attempt to minimize the creation of such novel epitopes because they may be immunogenic in humans.

There are few established methodologies designed to explore the potential immunogenicity of a recombinant protein. The present invention circumvents this problem and allows prediction of protein immunogenicity.

REFERENCES

Esmon P. C., Mitra I., Fournel M. A. 1988; Recombinant Factor VIII Immunogenicity studies. FASEBJ 2(5)5027.

Pannel R., Johnson D., Travis J. 1974; Biochemistry 13:5439–5445.

Rosenberg S., Barr P. J., Najarian R. C. and Hallewell R. A. 1984; Synthesis in yeast of a functional oxidation-resistant mutant of human Alpha-1-antitrypsin. Nature 312:77–80.

Courtney M., Buchwalder A., Tessier L. H., Jaye M., Benevente A., Balland A., Kohli V., Lathe R., Tolstoshev P. and Lecocq J. P., 1984; High-level production of biologically active human Alpha-1-antitrypsin in *Escherichia coli*. Proc. Nat. Acad. Sci. 81:669–673.

Courtney M., Jallat S., Tessier L. H., Benevente A., Crystal R. G. and Lecocq J. P. 1985; Synthesis in *E. coli* of Alpha-1-antitrypsin variants of therapeutic potential for emphysema and thrombosis. Nature 313:149–151.

Travis J., Rosenberg S., Barr P., Hallewell R., Owen M., George P. and Carrell R. 1985; Isolation and properties of human Alpha-1-Proteinase Inhibitor variants produced in yeast. J. Biol. Chem 260:4384–4389.

Janoff A., George-Nascimento C. and Rosenberg S. 1986; A. genetically engineered mutant human Alpha-1-Proteinase-Inhibitor is more resistant then the normal inhibitor to oxidative inactivation by chemicals, enzymes, cell and cigarette smoke. Am. Rev. Respir. Dis. 133:400–408.

Coan M. H., Brockway W. J., Equizabel A., Kreig T. and Fournel M. A. 1985; Preparation and properties of Alpha-1-Proteinase Inhibitor concentrate from human plasma. Vox Sang 48:333–342.

Glaser C. B., Chamomorro M., Crowley R., Karic L. J., Childes A. and Calderon M. 1982; The isolation of Alpha-1-proteinase inhibitor by a unique procedure designed for industrial application. Analytical Biochemistry 124:364–371.

Revak S. D., Rice C. L., Schraufstatter I. U., Halsey Jr. W. A., Boh B. P., Clancy R. M. and Cochrane C. G. 1985; Experimental pulmonary inflammatory injury in the monkey. J. Clin. Inves. 76:1182–1192.

Laemmli V. K. 1970; Cleavage of structural proteins during the assembly of the head of bacteriophage $T_4$. Nature 227:680–685.

Morrissey J. H. 1981; Silver stain for proteins in polyacrylamide gels: a modified procedure with enhanced uniform sensitivity. Analytical Biochemistry 117:307–310.

Ovary Z., 1958; Prog. Allergy 5:459–508.

Renart J., Reiser R. and Startk G. R. 1979. Transfer of proteins from gels to DMB paper and detection with antisera: a method for studying antibody specificity and structure. Proc. Nat. Acad. Sci. 76:3116.

Gervoy J. S., et al, 1977; Methods in Immunol 445–458.

Sharon N. 1980; Carbohydrates. Sci Ameri. 243:90–116.

Towbin H. and Gordon J. 1981; J. Immunol. Meth. 72:313–340.

Rotblat F., Goodall A. H., O'Brien D. P., Rawlings E., Middleton S., Tuddenham E. G. D.: Monoclonal antibodies to human procoagulant Factor VIII. J. Lab. Clin. Med. 101:736, 1983

Wood W. I., Capon D. J., Simonsen C. C., Eaton D. L., Gitschier J., Keyt B., Seeburg P. H., Smith D. H. Hollingshead P., Wion K. L. Dewart E., Tuddenham E. G. D., Vehar G. A., Lawn R. M.: Expression of active human factor VIII from recombinant DNA clones. Nature 312:330, 1984

Towbin H., Stehelin T., Gordon J.: Electrophoretic transfer of proteins from polyacrylamide gels to nitrocellulose sheets: procedure and some application. Proc. Nat'l. Acad. Sci. 76:4350, 1979.

Eng J., Reichlin M.: Fractionation of rabbit anti-horse cytochrome c-I. Mol. Immunol. 16:225, 1979

Jemmerson R., Margoliash E.: Topographic antigenic determinants on cytochrome c. J. Biol. Chem. 254:12706, 1979

Kamiyama T.: Immunological cross-reactions and species-specificities of bovine, goat and sheep serum albumins Immunochemistry 14:85, 1977

Sakata S., Atassi M. Z.: Immunochemistry of serum albumin. VI. A dynamic approach to the immunochemical cross-reactions of proteins using serum albumins from various species as models. Biochimica et Biophysica Acta 576:322, 1979

Berzofsky J. A.: Intrinsic and extrinsic factors in protein antigenic structure. Science 229:932, 1985

Kirwin K. S., Roberts H.: Current concepts on the management of inhibitors to Factor VIII, in Seghatchian M. J. (ed): Factor VIII—von Willebrand Factor, vol 2. Boca Raton, CRC, 1989, p. 157.

Pittman D. D., Kaufman R. J.: Structure-function relationships of Factor VIII elucidated through recombinant DNA technology. Thromb Haemostas 61:161, 1989

Toole J. J., Knopf J. L., Wozney J. M., Sultzman L. A., Buecker J. L., Pittman D. D., Kaufman R. J., Brown E., Shoemaker C., Orr E. C., Amphlett G. W., Foster W. B., Coe M. L., Knutson G. J., Fass D. N., Hewick R. M.: Molecular cloning of a cDNA encoding human antihemophilic factor. Nature 312:342, 1984

Vehar G. A., Keyt B., Eaton D., Rodriquez H., O'-Brien D. P., Rotblat F., Oppermann H., Keck R., Wood W. I., Harkins R. N., Tuddenham E. D. G., Lawn R. M., Capon D. J.: Structure of human Factor VIII. Nature 312:337, 1984

Fulcher C. A., Roberts J. R., Zimmerman T. S.: Thrombin proteolysis of purified Factor VIII procoagulation protein: correlations of activation with generation of a specific polypeptide. Blood 61:807, 1983

Eaton D. L., Hass P. E., Riddle L., Mather J., Wiebe M., Gregory T., Vehar G. A.: Characterization of recombinant human Factor VIII. J. Biol. Chem. 262:3285, 1987

Eaton, D., Rodriques H., Vehar G. A.: Proteolytic processing of human Factor VIII. Correlations of specific cleavages by thrombin, Factor Xa and activated protein C with activation and inactivation of Factor VIII coagulant activity. Biochemistry 25:505, 1986

Fay P. J.: Subunit structure of thrombin-activated human Factor VIIIa. Biochimica et Biophysica Acta 952:181, 1988

Pancham N., Dumas M., Madanat M. S., Esmon P. C., Voehringer V.: Recombinant and plasma FVIII share epitopes recognized by a panel of monoclonal and polyclonal antibodies. Thromb Haemostasis 58:340, 19 (abst)

Bloom J. W.: The interaction of rFNA Factor VIII, Factor VIII$_{des-797-1562}$ and Factor VIII$_{des-797-1562}$-derived peptides with phospholipid. Thromb Res. 48:439, 1987

Giles A. R., Tinlin S., Hoogendoorn H., Fournel M. A., Ng P., Pancham N.: In vivo characterization of recombinant Factor VIII in a canine model of hemophilia A (Factor VIII deficiency). Blood 72:335, 1988

Eaton D. L., Wood W. I., Eaton D., Hass P. E., Hollingshead P., Wion K., Mather J., Lawn R. M., Vehar G. A., Gorman C.: Construction and characterization of an active Factor VIII variant lacking the central one-third of the molecule. Biochemistry 25:8343, 1986

Toole J. J., Pittman D. D., Orr E. C., Murtha P., Wasley L. C., Kaufman, R. J.: A large region ($\simeq$95 kDa) of human factor VIII is dispensable for in vitro procoagulant activity. Proc. Nat'l Acad. Sci. 83:5939, 1986

Sarver N., Ricca G. A., Link J., Nathan M. H., Newman J., Drohan W. N.: Stable expression of recombinant Factor VIII molecules using a bovine papillomavirus vector. DNA 6:553, 1987

Meulien P., Faure T., Mischler F., Harrer H., Ulrich P., Bouderbala B., Dott K., Sainte Marie M., Mazurier C., Wiesel M-l., Van de Pol H., Cazenave J-P., Courtney M., Pavirani A.: A new recombinant procoagulation protein derived from the cDNA encoding human factor VIII. Protein Engineering 2:301, 1988

Langner K. D., Bird R. E., McCandliss R., Huber B., Amann E., Zettlemeissl G., Kupper H. A.: Synthesis of biologically active deletion mutants of human factor VIII:C. Behring Inst. Mitt. 82:16, 1988 van de Rijn, I., Zabriskie J. B., McCarthy M.: Group A streptococcal antigens cross-reactive with myocardium. J. Exp. Med. 146:579, 1977

Khoury E. L., Ritacco V., Cossio P. M., Laguens R. P., Szarfman A., Diez C., Arana R. M.: Circulating antibodies to peripheral nerve in American trypanosomiasis (Chagas' disease). Clin. Exp. Immunol. 36:8, 1979

Wood J. N., Hudson L., Jessell T. M., Yamamoto M.: A monoclonal antibody defining antigen determinants on subpopulations of mammalian neurons and Trypanosoma cruzi parasites. Nature 296:34, 1982

Kaplan S. L., August G. P., Blethen S. L., Brown D. R., Hintz R. L., Johansen A., Plotnick L. P., Underwood L. E., Bell J. J., Blizzard R. M., Foley T. P., Hopwood N. J., Kirkland R. T., Rosenfeld R. G., Van Wjk J. J.: Clinical studies with recombinant-DNA-derived methionyl human growth hormone in growth hormone deficient children. Lancet 1:697, 1986

Takano K., Shizume K.: Current clinical trials with authentic recombinant human growth hormone in Japan. Acta Paediatr Scand 325:93, 1986

Jones G. J., Intri L. M.: Safety and tolerance of recombinant interferon alfa-2a (Roferon ®-A) in cancer patients. Cancer 57:1709, 1986

Spiegel R. J., Spicehandler J. R., Jacobs S. L., Oden E. M.: Low incidence of serum neutralizing factors in patients receiving recombinant alfa-2b interferon (Intron A). Am J Med 80:223, 1986

Konrad M. W., Childs A. L., Merigan T. C., Borden E. C.: Assessment of the antigenic response in humans to a recombinant mutant interferon beta. J Clin Immunol 7:365, 1987

Pharmacia Fine Chemicals: Affinity Chromatography. Sweden, Lyungföretagen AB. 1979

Roy S. K., McGregor W. C., Orichowskj S. T.: Automated high-performance immunosorbent assay for recombinant leukocyte A interferon. J Chromat 327:189, 1985

Patek A. J., Taylor F. H. L.: J Clin Invest 16:113, 1937

Rick M. E., Wampler D. E., Hoyer L. W.: Rabbit Factor VIII:Identification of size heterogeneity. Blood 49:209, 1977

Prager E. M., Welling G. W., Wilson A. C.: Comparison of various Immunological methods for distinguishing among mammalian pancreatic ribonucleases of known amino acid sequence. J Mol Evol 10:293, 1978

Engvall E.: Enzyme immunoassay ELISA and EMIT. Meth Enzymol 70:419, 1980

What is claimed is:

1. A method of evaluating the immunogenic potential of recombinant Factor VIII in comparison to plasma-derived Factor VIII, comprising:
    (a) raising antibodies to recombinant Factor VIII in an animal;
    (b) isolating the antibodies in an antibody preparation;
    (c) removing from the antibody preparation, by affinity chromatography, any and all antibodies to plasma-derived Factor VIII to produce a depleted antibody preparation; and
    (d) separately reacting the depleted antibody preparation with recombinant Factor VIII and plasma-derived Factor VIII, whereby a positive-reaction with recombinant Factor VIII and not with plasma-derived Factor VIII indicates that recombinant Factor VIII elicits antibody not recognizing plasma-derived Factor VIII, thereby indicating that recombinant Factor VIII can potentially cause an immunological reaction in humans.

2. A method of evaluating the immunogenic potential of a fragment of an intact protein comprising:
    (a) raising antibodies to the fragment in an animal;
    (b) isolating the antibodies in an antibody preparation;
    (c) removing from the antibody preparation, by affinity chromatography, any and all antibodies to the intact protein to produce a depleted antibody preparation; and
    (d) separately reacting the depleted antibody preparation with the fragment and the intact protein, whereby a positive reaction with the fragment and not with the intact protein indicates that the fragment elicits antibody not recognizing the intact protein, thereby indicating that the fragment can potentially cause an immunological reaction in humans.

3. The method of claim 2 wherein the fragment is a fragment of Factor VIII.

4. A method of evaluating the immunogenic potential of recombinant alpha-1-proteinase inhibitor in comparison to a naturally occurring plasma-derived alpha-1-proteinase inhibitor, comprising:

(a) raising antibodies to recombinant alpha-1-proteinase inhibitor in an animal;
(b) isolating the antibodies in an antibody preparation;
(c) removing from the antibody preparation, by affinity chromatography, any and all antibodies to plasma-derived alpha-1-proteinase inhibitor to produce a depleted antibody preparation; and
(d) separately reacting the depleted antibody preparation with recombinant alpha-1-proteinase inhibitor and plasma-derived alpha-1-proteinase inhibitor, whereby a positive reaction with recombinant alpha-1-proteinase inhibitor and not with plasma-derived alpha-1-proteinase inhibitor indicates that recombinant alpha-1-proteinase inhibitor elicits antibody not recognizing plasma-derived alpha-1-proteinase inhibitor, thereby indicating that recombinant alpha-1-proteinase inhibitor can potentially cause an immunological reaction in humans.

5. A method for evaluating the immunogenic potential of a variant of a naturally occurring protein, comprising:
(a) raising antibodies to the variant in an animal;
(b) isolating the antibodies in an antibody preparation;
(c) removing from the antibody preparation, by affinity chromatography, any and all antibodies to the naturally occurring protein to produce a depleted antibody preparation; and
(d) separately reacting the depleted antibody preparation with the variant and the naturally occurring protein, whereby a positive reaction with the variant and not with the naturally occurring protein indicates that the variant elicits antibody not recognizing the naturally occurring protein, thereby indicating that the variant can potentially cause an immunological reaction in humans.

6. The method of claim 5 wherein the variant is a variant of alpha-1-proteinase inhibitor.

* * * * *